(12) United States Patent
Walborn et al.

(10) Patent No.: US 10,391,211 B2
(45) Date of Patent: Aug. 27, 2019

(54) NEGATIVE PRESSURE WOUND THERAPY ORTHOPEDIC DEVICE

(71) Applicant: Ossur Iceland ehf, Reykjavik (IS)

(72) Inventors: Jonathan Walborn, Mission Viejo, CA (US); Janaki Ram-srinivasaRao Chetlapalli, Irvine, CA (US); Gudni Ingimarsson, Reykjavik (IS)

(73) Assignee: Ossur Iceland ehf, Reykjavik (IS)

( * ) Notice: Subject to any disclaimer, the term of this patent is extended or adjusted under 35 U.S.C. 154(b) by 626 days.

(21) Appl. No.: 15/006,278

(22) Filed: Jan. 26, 2016

(65) Prior Publication Data

US 2016/0213823 A1  Jul. 28, 2016

Related U.S. Application Data

(60) Provisional application No. 62/107,636, filed on Jan. 26, 2015.

(51) Int. Cl.
*A61M 1/00* (2006.01)
*A61F 5/01* (2006.01)
(Continued)

(52) U.S. Cl.
CPC ......... *A61M 1/0088* (2013.01); *A61F 5/0102* (2013.01); *A61F 5/0111* (2013.01);
(Continued)

(58) Field of Classification Search
CPC .................. A61F 5/0102; A61F 5/0111; A61F 13/00068; A61F 13/0216; A61M 1/0023;
(Continued)

(56) References Cited

U.S. PATENT DOCUMENTS 975,576 A    11/1910 Sexton
1,012,017 A   12/1911 Salt
(Continued)

FOREIGN PATENT DOCUMENTS

CN    101711141 A    5/2010
CN    102026592 A    4/2011
(Continued)

OTHER PUBLICATIONS

International Search Report and Written Opinion for corresponding International Application No. PCT/US2014/056201, dated Dec. 5, 2014.
(Continued)

*Primary Examiner* — Benjamin J Klein
(74) *Attorney, Agent, or Firm* — Workman Nydegger

(57) ABSTRACT

A negative pressure wound therapy (NPWT) orthopedic device includes a base shell and a dorsal shell contoured to generally correspond to an opening of the base shell. The dorsal shell includes a proximal section and a distal section. The proximal section at least in part defines a receiving space. A NPWT system includes a pump mechanism secured in the receiving space and a wound covering situated inside of the base shell and arranged to form a sealed volume over a wound area of a user. At least one conduit forms a fluid connection between the wound covering and the pump mechanism. The pump mechanism is arranged to apply a negative pressure to the wound area through the at least one conduit.

11 Claims, 8 Drawing Sheets

(51) Int. Cl.
*A61F 13/00* (2006.01)
*A61F 13/02* (2006.01)

(52) U.S. Cl.
CPC .... *A61F 13/00068* (2013.01); *A61F 13/0216* (2013.01); *A61M 1/0023* (2013.01); *A61M 2209/088* (2013.01); *A61M 2210/086* (2013.01)

(58) Field of Classification Search
CPC .......... A61M 1/0088; A61M 2209/088; A61M 2210/086
See application file for complete search history.

(56) References Cited

U.S. PATENT DOCUMENTS

| | | |
|---|---|---|
| 2,200,849 A | 5/1940 | Margolin |
| 2,236,367 A | 3/1941 | Gruber |
| 2,292,297 A | 8/1942 | Sherlock |
| 2,444,640 A | 7/1948 | Epstein |
| 2,868,191 A | 1/1959 | Juhasz |
| 2,885,797 A | 5/1959 | Chrencik |
| 2,888,016 A | 5/1959 | De Lamater |
| 2,909,854 A | 10/1959 | Edelstein |
| 2,913,837 A | 11/1959 | Geuder |
| 2,917,844 A | 12/1959 | Scholl |
| 2,928,193 A | 3/1960 | Kristan |
| 2,979,835 A | 4/1961 | Scholl |
| 2,979,836 A | 4/1961 | Scholl |
| 3,270,358 A | 9/1966 | Milner |
| 3,464,126 A | 9/1969 | Sarkissian |
| 3,548,420 A | 12/1970 | Spence |
| 3,580,248 A | 5/1971 | Larson |
| 3,681,860 A | 8/1972 | Bidegain |
| 3,685,176 A | 8/1972 | Rudy |
| 3,730,169 A | 5/1973 | Fiber |
| 3,735,758 A | 5/1973 | Novotney |
| 3,760,056 A | 9/1973 | Rudy |
| 3,786,805 A | 1/1974 | Tourin |
| 3,792,537 A | 2/1974 | Plank et al. |
| 3,814,088 A | 6/1974 | Raymond |
| 3,834,377 A | 9/1974 | Lebold |
| 3,859,740 A | 1/1975 | Kemp |
| 3,922,800 A | 12/1975 | Miller et al. |
| 3,955,565 A | 5/1976 | Johnson, Jr. |
| 4,045,888 A | 9/1977 | Oxenberg |
| 4,057,056 A | 11/1977 | Payton |
| 4,095,353 A | 6/1978 | Foldes |
| 4,100,686 A | 7/1978 | Sgarlato et al. |
| 4,142,307 A | 3/1979 | Martin |
| 4,177,583 A | 12/1979 | Chapman |
| 4,184,273 A | 1/1980 | Boyer et al. |
| 4,217,706 A | 8/1980 | Vartanian |
| 4,217,893 A | 8/1980 | Payton |
| 4,232,459 A | 11/1980 | Vaccari |
| 4,237,626 A | 12/1980 | Brown |
| 4,267,649 A | 5/1981 | Smith |
| 4,300,294 A | 11/1981 | Riecken |
| 4,333,248 A | 6/1982 | Samuels |
| 4,370,818 A | 2/1983 | Simoglou |
| 4,408,402 A | 10/1983 | Looney |
| 4,414,965 A | 11/1983 | Mauldin et al. |
| D272,281 S | 1/1984 | Alush |
| 4,446,856 A | 5/1984 | Jordan |
| 4,494,536 A | 1/1985 | Latenser |
| 4,505,269 A | 3/1985 | Davies et al. |
| 4,550,721 A | 11/1985 | Michel |
| 4,565,017 A | 1/1986 | Ottieri |
| 4,571,853 A | 2/1986 | Medrano |
| 4,572,169 A | 2/1986 | Mauldin et al. |
| 4,587,962 A | 5/1986 | Greene et al. |
| 4,598,484 A | 7/1986 | Ma |
| 4,599,811 A | 7/1986 | Rousseau |
| 4,608,768 A | 9/1986 | Cavanagh |
| 4,620,378 A | 11/1986 | Sartor |
| 4,633,598 A | 1/1987 | Moronaga et al. |
| 4,633,599 A | 1/1987 | Morell et al. |
| 4,633,877 A | 1/1987 | Pendergast |
| 4,660,300 A | 4/1987 | Morell et al. |
| 4,669,202 A | 6/1987 | Ottieri |
| 4,674,204 A | 6/1987 | Sullivan et al. |
| 4,674,205 A | 6/1987 | Anger |
| 4,677,767 A | 7/1987 | Darby |
| 4,680,878 A | 7/1987 | Pozzobon et al. |
| 4,689,898 A | 9/1987 | Fahey |
| 4,719,710 A | 1/1988 | Pozzobon |
| 4,727,661 A | 3/1988 | Kuhn |
| 4,741,115 A | 5/1988 | Pozzobon |
| 4,748,726 A | 6/1988 | Schoch |
| 4,760,653 A | 8/1988 | Baggio |
| 4,771,768 A | 9/1988 | Crispin |
| 4,773,170 A | 9/1988 | Moore et al. |
| 4,793,078 A | 12/1988 | Andrews |
| D299,787 S | 2/1989 | Bates |
| 4,805,321 A | 2/1989 | Tonkel |
| 4,805,601 A | 2/1989 | Eischen, Sr. |
| 4,811,504 A | 3/1989 | Bunke |
| 4,869,001 A | 9/1989 | Brown |
| 4,872,273 A | 10/1989 | Smeed |
| 4,879,822 A | 11/1989 | Hayes |
| 4,893,418 A | 1/1990 | Ogden |
| 4,934,355 A | 6/1990 | Porcelli |
| 4,947,838 A | 8/1990 | Giannetti |
| 4,974,583 A | 12/1990 | Freitas |
| 5,065,481 A | 11/1991 | Walkhoff |
| 5,065,531 A | 11/1991 | Prestridge |
| 5,078,128 A | 1/1992 | Grim et al. |
| 5,123,180 A | 6/1992 | Nannig et al. |
| 5,125,400 A | 6/1992 | Johnson, Jr. |
| D329,527 S | 9/1992 | Cohen |
| 5,143,058 A | 9/1992 | Luber et al. |
| D330,109 S | 10/1992 | Hatfield |
| 5,152,038 A | 10/1992 | Schoch |
| 5,154,682 A | 10/1992 | Kellerman |
| 5,154,695 A | 10/1992 | Farris et al. |
| 5,157,813 A | 10/1992 | Carroll |
| 5,176,623 A | 1/1993 | Stetman et al. |
| 5,176,624 A | 1/1993 | Kuehnreich |
| 5,183,036 A | 2/1993 | Spademan |
| 5,197,942 A | 3/1993 | Brady |
| D334,646 S | 4/1993 | Dissinger |
| D337,876 S | 8/1993 | Kilbey |
| 5,233,767 A | 8/1993 | Kramer |
| 5,242,379 A | 9/1993 | Harris et al. |
| 5,257,470 A | 11/1993 | Auger et al. |
| 5,277,695 A | 1/1994 | Johnson, Jr. et al. |
| D344,589 S | 2/1994 | Kilbey |
| 5,288,286 A | 2/1994 | Davis et al. |
| 5,325,613 A | 7/1994 | Sussmann |
| 5,329,705 A | 7/1994 | Grim et al. |
| D352,191 S | 11/1994 | Zorian |
| D352,784 S | 11/1994 | Cohen et al. |
| 5,359,791 A | 11/1994 | Prahl et al. |
| 5,368,549 A | 11/1994 | McVicker |
| 5,368,551 A | 11/1994 | Zuckerman |
| 5,370,133 A | 12/1994 | Darby et al. |
| 5,378,223 A | 1/1995 | Grim et al. |
| 5,399,152 A | 3/1995 | Habermeyer et al. |
| 5,407,421 A | 4/1995 | Goldsmith |
| 5,425,701 A | 6/1995 | Oster et al. |
| 5,426,872 A | 6/1995 | Hayes |
| 5,429,377 A | 7/1995 | Duer |
| 5,429,588 A | 7/1995 | Young et al. |
| 5,433,695 A | 7/1995 | Drennan |
| 5,435,009 A | 7/1995 | Schild et al. |
| 5,438,768 A | 8/1995 | Bauerfeind |
| 5,441,015 A | 8/1995 | Farley |
| D363,780 S | 10/1995 | Darby et al. |
| 5,464,385 A | 11/1995 | Grim |
| 5,477,593 A | 12/1995 | Leick |
| D365,919 S | 1/1996 | Chen |
| 5,483,757 A | 1/1996 | Frykberg |
| 5,496,263 A | 3/1996 | Fuller, II et al. |
| 5,548,848 A | 8/1996 | Huybrechts |

(56) References Cited

U.S. PATENT DOCUMENTS

| | | |
|---|---|---|
| D373,548 S | 9/1996 | Losi, II |
| 5,558,627 A | 9/1996 | Singer et al. |
| D375,191 S | 11/1996 | Tonkel et al. |
| 5,577,998 A | 11/1996 | Johnson, Jr. et al. |
| D376,429 S | 12/1996 | Antar |
| 5,617,650 A | 4/1997 | Grim |
| D379,258 S | 5/1997 | Cheng |
| 5,641,322 A | 6/1997 | Silver et al. |
| 5,647,104 A | 7/1997 | James |
| 5,656,226 A | 8/1997 | McVicker |
| D383,250 S | 9/1997 | Amico |
| D384,746 S | 10/1997 | Varn |
| D390,345 S | 2/1998 | Aird et al. |
| 5,717,996 A | 2/1998 | Feldmann |
| D391,748 S | 3/1998 | Koh |
| 5,761,834 A | 6/1998 | Grim et al. |
| 5,778,563 A | 7/1998 | Ahlbaumer |
| 5,778,565 A | 7/1998 | Holt et al. |
| 5,797,862 A | 8/1998 | Lamont |
| D398,142 S | 9/1998 | Benoit |
| D398,439 S | 9/1998 | McDonald |
| 5,819,378 A | 10/1998 | Doyle |
| 5,827,210 A | 10/1998 | Antar et al. |
| 5,827,211 A | 10/1998 | Sellinger |
| D401,042 S | 11/1998 | Davis |
| 5,833,639 A | 11/1998 | Nunes et al. |
| 5,836,902 A | 11/1998 | Gray |
| 5,846,063 A | 12/1998 | Lakic |
| 5,853,380 A | 12/1998 | Miller |
| 5,857,987 A | 1/1999 | Habermeyer |
| D404,895 S | 2/1999 | Rosato |
| 5,868,690 A | 2/1999 | Eischen, Sr. |
| 5,913,841 A | 6/1999 | Lamont |
| 5,934,599 A | 8/1999 | Hammerslag |
| 5,951,504 A | 9/1999 | Iglesias et al. |
| 5,961,477 A | 10/1999 | Turtzo |
| 5,993,404 A | 11/1999 | Mc Niel |
| 6,000,148 A | 12/1999 | Cretinon |
| D418,967 S | 1/2000 | Stengel |
| 6,021,780 A | 2/2000 | Darby |
| 6,027,468 A | 2/2000 | Pick |
| 6,044,578 A | 4/2000 | Kelz |
| 6,098,315 A | 8/2000 | Hoffmann, III |
| 6,131,195 A | 10/2000 | Foreman |
| 6,202,953 B1 | 3/2001 | Hammerslag |
| 6,205,685 B1 | 3/2001 | Kellerman |
| D440,754 S | 4/2001 | Bathum |
| 6,228,044 B1 | 5/2001 | Jensen et al. |
| 6,267,742 B1 | 7/2001 | Krivosha et al. |
| RE37,338 E | 8/2001 | McVicker |
| 6,289,558 B1 | 9/2001 | Hammerslag |
| 6,334,854 B1 | 1/2002 | Davis |
| 6,338,768 B1 | 1/2002 | Chi |
| 6,361,514 B1 | 3/2002 | Brown et al. |
| 6,377,178 B1 | 4/2002 | Detoro et al. |
| 6,409,691 B1 | 6/2002 | Dakin et al. |
| D461,936 S | 8/2002 | Fiorini et al. |
| 6,432,073 B2 | 8/2002 | Pior et al. |
| D467,708 S | 12/2002 | Portzline |
| D473,654 S | 4/2003 | Iglesias et al. |
| D473,704 S | 4/2003 | Wilson |
| 6,572,571 B2 | 6/2003 | Lowe |
| D476,799 S | 7/2003 | Fuerst |
| 6,589,194 B1 | 7/2003 | Calderon et al. |
| 6,682,497 B2 | 1/2004 | Jensen et al. |
| 6,755,798 B2 | 6/2004 | McCarthy et al. |
| 6,792,699 B2 | 9/2004 | Long et al. |
| D500,855 S | 1/2005 | Pick et al. |
| 6,866,043 B1 | 3/2005 | Davis |
| D504,005 S | 4/2005 | Schoenborn et al. |
| D505,727 S | 5/2005 | Krahner et al. |
| 6,945,944 B2 | 9/2005 | Kuiper et al. |
| 6,976,972 B2 | 12/2005 | Bradshaw |
| 6,991,613 B2 | 1/2006 | Sensabaugh |
| D517,306 S | 3/2006 | Hoeft |
| 7,010,823 B2 | 3/2006 | Baek |
| 7,018,351 B1 | 3/2006 | Iglesias et al. |
| D523,217 S | 6/2006 | Matis et al. |
| D528,214 S | 9/2006 | Binet |
| 7,198,610 B2 | 4/2007 | Ingimundarson et al. |
| 7,281,341 B2 | 10/2007 | Reagan et al. |
| 7,288,076 B2 | 10/2007 | Grim et al. |
| D554,835 S | 11/2007 | Peydro |
| D555,291 S | 11/2007 | Danzo |
| D555,343 S | 11/2007 | Bettencourt |
| 7,303,538 B2 | 12/2007 | Grim et al. |
| 7,311,686 B1 | 12/2007 | Iglesias et al. |
| 7,354,411 B2 | 4/2008 | Perry et al. |
| RE40,363 E | 6/2008 | Grim et al. |
| 7,384,584 B2 | 6/2008 | Jerome et al. |
| D575,039 S | 8/2008 | Amado et al. |
| D576,781 S | 9/2008 | Chang et al. |
| 7,418,755 B2 | 9/2008 | Bledsoe et al. |
| D583,544 S | 12/2008 | Fuerst |
| D583,956 S | 12/2008 | Chang et al. |
| 7,493,706 B2 | 2/2009 | Cho et al. |
| 7,524,295 B1 | 4/2009 | Peters et al. |
| D592,755 S | 5/2009 | Chang et al. |
| D592,756 S | 5/2009 | Chang et al. |
| D594,368 S | 6/2009 | Butler |
| D596,301 S | 7/2009 | Campos et al. |
| D596,386 S | 7/2009 | Brambilla |
| 7,591,050 B2 | 9/2009 | Hammerslag |
| D603,155 S | 11/2009 | Della Valle et al. |
| D614,775 S | 4/2010 | Snively |
| D615,285 S | 5/2010 | Martin |
| D616,556 S | 5/2010 | Hu |
| 7,717,869 B2 | 5/2010 | Eischen, Sr. |
| 7,727,174 B2 | 6/2010 | Chang et al. |
| D622,494 S | 8/2010 | Warren |
| 7,838,717 B2 | 11/2010 | Haggstrom et al. |
| D634,438 S | 3/2011 | Hu |
| D634,852 S | 3/2011 | Hu |
| D636,157 S | 4/2011 | Nascimento |
| D636,159 S | 4/2011 | Petrie |
| 7,964,766 B2 | 6/2011 | Blott et al. |
| D642,363 S | 8/2011 | Rajmohan et al. |
| D642,775 S | 8/2011 | Raysse |
| 8,002,724 B2 | 8/2011 | Hu et al. |
| 8,012,112 B2 | 9/2011 | Barberio |
| 8,021,347 B2 | 9/2011 | Vitaris et al. |
| D648,113 S | 11/2011 | Chang |
| RE43,063 E | 1/2012 | Kim |
| D651,381 S | 1/2012 | Simms |
| 8,158,844 B2 * | 4/2012 | McNeil ............... A61M 1/0088 602/42 |
| D661,887 S | 6/2012 | Petrie |
| 8,308,705 B2 | 11/2012 | Lin et al. |
| 8,313,449 B2 | 11/2012 | Hardman et al. |
| D675,421 S | 2/2013 | Petrie |
| D677,866 S | 3/2013 | Vestuti et al. |
| D680,728 S | 4/2013 | Stryjak |
| D682,517 S | 5/2013 | Taylor |
| D683,214 S | 5/2013 | McAdam |
| D684,760 S | 6/2013 | Williams, Jr. |
| 8,506,510 B2 | 8/2013 | Hu et al. |
| D689,677 S | 9/2013 | Bathum et al. |
| 8,574,181 B2 | 11/2013 | Bird et al. |
| D696,499 S | 12/2013 | Lehtinen |
| D696,785 S | 12/2013 | Weaver, II et al. |
| D698,074 S | 1/2014 | Hargreaves |
| D698,338 S | 1/2014 | Ingham et al. |
| D700,404 S | 2/2014 | Niefer |
| D701,032 S | 3/2014 | Leleu |
| D701,033 S | 3/2014 | Leleu |
| D703,335 S | 4/2014 | Bird et al. |
| D709,277 S | 7/2014 | Takenaka |
| D712,639 S | 9/2014 | Spring |
| D714,042 S | 9/2014 | Petrie |
| 9,003,677 B2 | 4/2015 | Goodsmith et al. |
| D729,393 S | 5/2015 | Dunn et al. |
| D740,896 S | 10/2015 | Halper, Jr. |
| D742,017 S | 10/2015 | Dunn et al. |
| D744,111 S | 11/2015 | Dunn et al. |

(56) References Cited

U.S. PATENT DOCUMENTS

| | | |
|---|---|---|
| 9,220,621 B2 | 12/2015 | Hu et al. |
| 9,220,622 B2 | 12/2015 | Ingimundarson et al. |
| 9,248,042 B2 | 2/2016 | Lopez et al. |
| 9,333,106 B2 | 5/2016 | Hu et al. |
| 9,468,553 B2 | 10/2016 | Hu et al. |
| D772,418 S | 11/2016 | Li et al. |
| 9,492,301 B2 | 11/2016 | Hu et al. |
| D776,288 S | 1/2017 | Dunn et al. |
| D776,289 S | 1/2017 | Dunn et al. |
| 9,668,907 B2 | 6/2017 | Romo et al. |
| 9,744,065 B2 | 8/2017 | Walborn et al. |
| 9,839,548 B2 | 12/2017 | Ingvarsson et al. |
| 9,839,549 B2 | 12/2017 | Walborn et al. |
| 9,839,550 B2 | 12/2017 | Walborn et al. |
| 2002/0095105 A1 | 7/2002 | Jensen |
| 2002/0095750 A1 | 7/2002 | Hammerslag |
| 2002/0128574 A1 | 9/2002 | Darby |
| 2003/0093882 A1 | 5/2003 | Gorza et al. |
| 2003/0171703 A1 | 9/2003 | Grim et al. |
| 2003/0204938 A1 | 11/2003 | Hammerslag |
| 2004/0010212 A1 | 1/2004 | Kuiper et al. |
| 2004/0019307 A1 | 1/2004 | Grim et al. |
| 2004/0167453 A1 | 8/2004 | Peters |
| 2005/0131324 A1 | 6/2005 | Bledsoe |
| 2005/0145256 A1 | 7/2005 | Howard et al. |
| 2005/0165338 A1 | 7/2005 | Iglesias et al. |
| 2005/0171461 A1 | 8/2005 | Pick |
| 2005/0172517 A1 | 8/2005 | Bledsoe et al. |
| 2005/0274046 A1 | 12/2005 | Schwartz |
| 2006/0084899 A1 | 4/2006 | Verkade et al. |
| 2006/0135899 A1 | 6/2006 | Jerome et al. |
| 2006/0135902 A1 | 6/2006 | Ingimundarson et al. |
| 2006/0156517 A1 | 7/2006 | Hammerslag et al. |
| 2006/0189907 A1 | 8/2006 | Pick et al. |
| 2006/0217649 A1 | 9/2006 | Rabe |
| 2006/0229541 A1 | 10/2006 | Hassler et al. |
| 2007/0055188 A1 | 3/2007 | Avni et al. |
| 2007/0167884 A1 | 7/2007 | Mangrum et al. |
| 2007/0169378 A1 | 7/2007 | Sodeberg et al. |
| 2007/0185425 A1 | 8/2007 | Einarsson et al. |
| 2007/0191749 A1 | 8/2007 | Barberio |
| 2007/0282230 A1 | 12/2007 | Valderrabano et al. |
| 2007/0293798 A1 | 12/2007 | Hu et al. |
| 2008/0060167 A1 | 3/2008 | Hammerslag et al. |
| 2008/0060168 A1 | 3/2008 | Hammerslag et al. |
| 2008/0066272 A1 | 3/2008 | Hammerslag et al. |
| 2008/0066345 A1 | 3/2008 | Hammerslag et al. |
| 2008/0066346 A1 | 3/2008 | Hammerslag et al. |
| 2008/0083135 A1 | 4/2008 | Hammerslag et al. |
| 2008/0294082 A1 | 11/2008 | Chang et al. |
| 2008/0294083 A1 | 11/2008 | Chang et al. |
| 2009/0012482 A1 | 1/2009 | Pinto et al. |
| 2009/0099495 A1 | 4/2009 | Campos et al. |
| 2009/0227927 A1 | 9/2009 | Frazer |
| 2009/0234260 A1* | 9/2009 | Coward .............. A61M 1/0023 601/148 |
| 2009/0270820 A1 | 10/2009 | Johnson et al. |
| 2009/0287127 A1 | 11/2009 | Hu et al. |
| 2009/0287128 A1 | 11/2009 | Ingimundarson et al. |
| 2010/0069808 A1 | 3/2010 | Mitchell |
| 2010/0100020 A1 | 4/2010 | Fout et al. |
| 2010/0234782 A1 | 9/2010 | Hu et al. |
| 2010/0324461 A1 | 12/2010 | Darby, II et al. |
| 2011/0009791 A1 | 1/2011 | Hopmann |
| 2011/0015555 A1 | 1/2011 | Anderson et al. |
| 2011/0196275 A1 | 8/2011 | Chang et al. |
| 2012/0010534 A1 | 1/2012 | Kubiak et al. |
| 2012/0035560 A1 | 2/2012 | Eddy et al. |
| 2012/0078148 A1 | 3/2012 | Hu et al. |
| 2012/0220960 A1 | 8/2012 | Ruland |
| 2012/0238924 A1 | 9/2012 | Avni |
| 2013/0066247 A1 | 3/2013 | Bird et al. |
| 2013/0310721 A1 | 11/2013 | Hu et al. |
| 2014/0128789 A1 | 5/2014 | Chen |
| 2014/0171837 A1 | 6/2014 | Harcourt |
| 2014/0276310 A1 | 9/2014 | Grim et al. |
| 2014/0350446 A1 | 11/2014 | Gunnsteinsson |
| 2015/0075030 A1 | 3/2015 | Walborn et al. |
| 2015/0164179 A1 | 6/2015 | Walborn et al. |

FOREIGN PATENT DOCUMENTS

| | | |
|---|---|---|
| DE | 23 416 58 A1 | 3/1974 |
| DE | 32 287 53 A1 | 2/1984 |
| EP | 0 095 396 A1 | 11/1983 |
| EP | 0 201 051 A1 | 11/1986 |
| EP | 0770368 A1 | 5/1997 |
| EP | 2468323 A1 | 6/2012 |
| FR | 2 399 811 A1 | 3/1979 |
| FR | 2634988 A1 | 2/1990 |
| FR | 2 681 516 A1 | 3/1993 |
| GB | 2 124 473 A | 2/1984 |
| GB | 2 178 940 A | 2/1987 |
| JP | 2005211626 A | 8/2005 |
| WO | 93/13685 A1 | 7/1993 |
| WO | 93/24081 A1 | 12/1993 |
| WO | 94/18863 A1 | 9/1994 |
| WO | 97/36507 A1 | 10/1997 |
| WO | 2004/021817 A1 | 3/2004 |
| WO | 2006035469 A2 | 4/2006 |
| WO | 2006045079 A1 | 4/2006 |
| WO | 2007078845 A2 | 7/2007 |
| WO | 2010104824 A1 | 9/2010 |
| WO | 2013/084213 A1 | 6/2013 |
| WO | 2015006766 A1 | 1/2015 |

OTHER PUBLICATIONS

International Search Report from PCT Application No. PCT/US2009/003018, dated Jul. 24, 2009.

Product Information Sheet: Nextep Contour Walker, Procare, DJ Orthopedics, Jan. 1, 2008, 1 page. Retrieved from the internet, www.djortho.com.

Product Information Sheet: Nextep Contour w/Air Walker, Procare, DJ Orthopedics, Jan. 1, 2008, 1 page. Retrieved from internet, www.djortho.com.

Product Information Sheet: XP Achilles Walker (EU only), Aircast, Jan. 1, 2008, 4 pages. Retrieved from the internet, http://www.aircast.com/index.asp/fuseaction/products.detail/cat/2/id/104.

Product Information Sheet: XP Diabetic Walker System, Aircast, Jan. 1, 2008, 4 pages. Retrieved from the internet, http://www.aircast.com/index.asp/fuseaction/products.detail/cat/2/id/15.

Product Information Sheet: SP Walker (short pneumatic), Aircast, Jan. 1, 2008, 4 pages. Retrieved from the internet, http://www.aircast.com/index.asp/fuseaction/products.detail/cat/2/id/14.

Product Information Sheet: FP Walker (foam pneumatic), Aircast, Jan. 1, 2008, 4 pages. Retrieved from the internet, http://www.aircast.com/index.asp/fuseaction/products.detail/cat/2/id/75.

Product Information Sheet: XP Walker (extra pneumatic), Aircast, Jan. 1, 2008, 4 pages. Retrieved from the internet, http://www.aircast.com/index.asp/fuseaction/products.detail/cat/2/id/76.

International Search Report and Written Opinion from International Application No. PCT/US2014/057421, dated Dec. 8, 2014.

International Search Report and Written Opinion from International Application No. PCT/US2014/069686, dated Mar. 13, 2015.

Chinese Office Action from CN Application No. 201480052921.0, dated Feb. 4, 2017.

International Search Report from PCT Application No. PCT/US2016/014816, dated Apr. 28, 2016.

European Search Report from corresponding European Application No. EP 15 20 0198.8, dated May 20, 2016.

\* cited by examiner

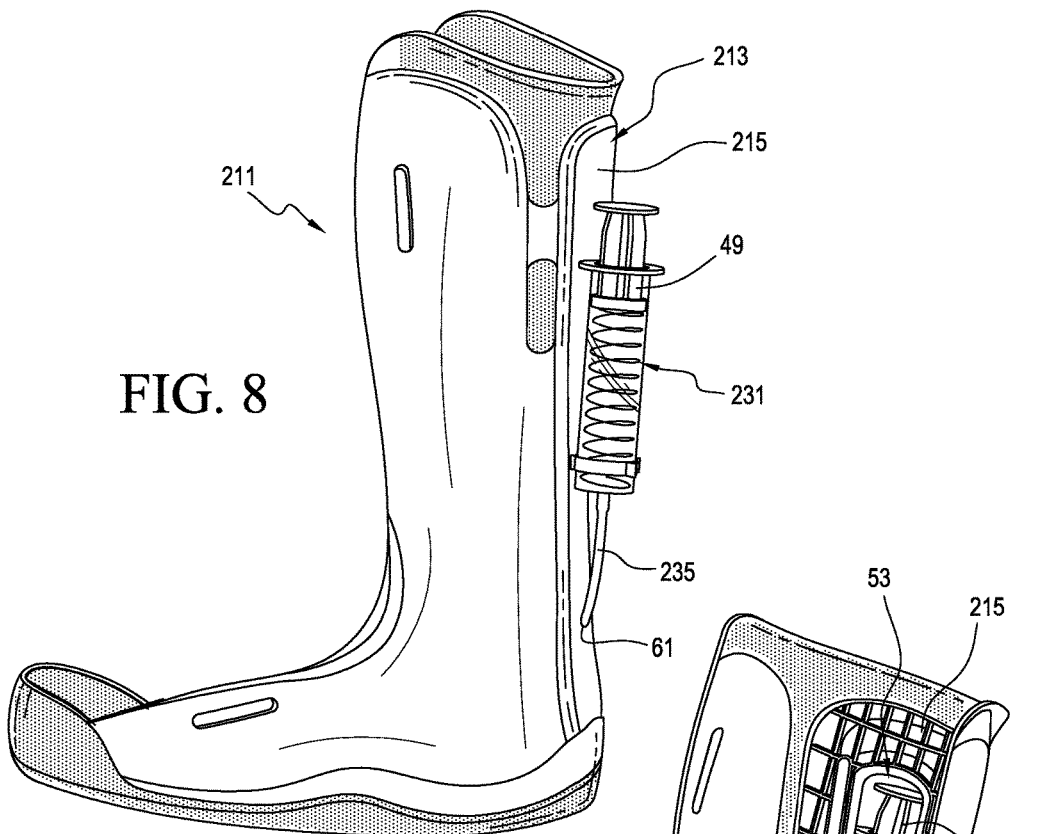
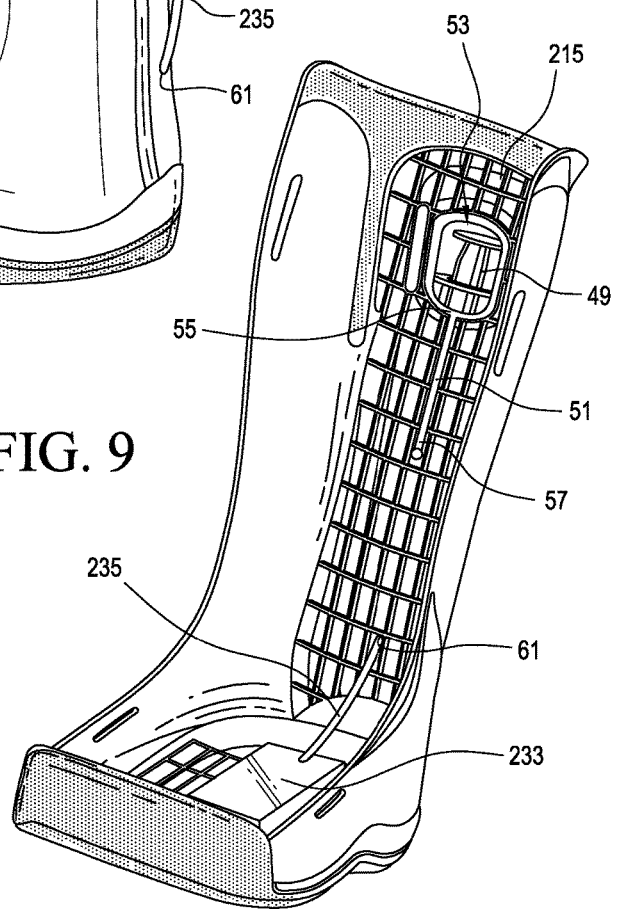

NEGATIVE PRESSURE WOUND THERAPY ORTHOPEDIC DEVICE

TECHNICAL FIELD

The disclosure relates to a negative pressure wound therapy orthopedic device.

BACKGROUND

Negative pressure wound therapy ("NPWT") systems are used to accelerate wound healing by applying a negative pressure to a wound. Generally, a NPWT system covers the wound with a flexible cover layer such as a polymeric film to establish a vacuum reservoir over the wound where a negative pressure may be applied. To allow the negative pressure to be maintained over time, the cover layer may include an adhesive property that forms a substantially fluid tight seal with the skin surrounding the wound. Most NPWT systems apply a negative pressure to the wound using an external vacuum source such that fluid communication must be established between the reservoir and the vacuum source. To this end, a fluid port is coupled to the cover layer to provide an interface for an exudate tube extending from the external vacuum source.

While such systems can accelerate wound healing, they tend to suffer from a number of drawbacks, especially for patients with lower limb injuries, such as pressure ulcers, surgical cuts/incisions, or amputations. For instance, known systems are often bulky and heavy, especially for use after a patient has been discharged from a hospital. Furthermore, these systems typically include an external vacuum source intended to be worn close the patient's waist, necessitating routing of the tube from the waist to the wound area on the lower limb. The tube can then become tangled or caught during use, disabling the NPWT system and/or injuring the patient.

The height of the vacuum source above the wound area also generates a fluid head height tending to act against the negative pressure applied at the wound area. In addition, movement of the patient's foot relative to the location of the system on the patient's waist can drastically vary the fluid head height, which, in turn, can vary the level of negative pressure applied at the wound area, producing unpredictable and even damaging effects.

SUMMARY

Embodiments of the NPWT orthopedic device provide accelerated wound healing by applying a negative pressure to a wound area. The NPWT orthopedic device includes a NPWT system having a pump mechanism and a wound covering situated inside the orthopedic device and arranged to form a sealed volume over the wound area. The wound covering is fluidly connected to the pump mechanism via a conduit. The pump mechanism includes a negative pressure source arranged to apply a negative pressure to the wound area under the wound covering. The negative pressure applied by the pump mechanism to the wound area can draw wound exudate and/or other secretions away from the wound area, helping to accelerate healing.

Embodiments of the disclosure integrate the pump mechanism on the posterior and/or anterior surfaces of the orthopedic device. By arranging the pump mechanism on the posterior and/or anterior surfaces of the orthopedic device, the distance between the pump mechanism and the wound area is generally constant and shortened as compared to an external vacuum source being carried near the hip or on other parts of the user's body as in the prior art, reducing the likelihood of the conduit 35 being tangled or caught during use.

The anterior or posterior positioning of the pump mechanism also beneficially reduces and stabilizes the effects of fluid head height within the NPWT system acting opposite the negative pressure applied by the pump mechanism, making the system more efficient and reliable. It also does not undesirably increase a width of either the medial or lateral aspects of the orthopedic device, reducing the likelihood of injury or discomfort the user.

According to an embodiment, a NPWT orthopedic device includes a base shell having a posterior portion and a plantar portion. The base shell defines an opening over a dorsal aspect thereof. A dorsal shell is contoured to generally correspond to the opening of the base shell. The dorsal shell includes a proximal section defining a receiving space and a distal section.

A NPWT system includes a pump mechanism secured in the receiving space, a wound covering situated inside of the base shell and arranged to form a sealed volume over a wound area of a user, and at least one conduit forming a fluid connection between the wound covering and the pump mechanism. The pump mechanism is arranged to apply a negative pressure to the wound area through the at least one conduit.

By arranging the pump mechanism within the receiving space on the dorsal shell, the pump mechanism is located inside the orthopedic device during use and protected from damage due to accidental contact with external objects. This also reduces the likelihood of tampering or unintended interference. In addition, the distance between the pump mechanism and the wound area is generally constant and shortened, reducing and stabilizing the effects of potentially counterproductive fluid head height within the NPWT system.

According to a variation, the receiving space is defined by a cover member removably attached over a cutout formed in the dorsal shell, providing access to the pump mechanism from the outside of the orthopedic device. This beneficially allows the pump mechanism to be removed, replaced, and/or maintained without having to remove the orthopedic device from the user's leg.

BRIEF DESCRIPTION OF THE DRAWINGS

These and other features, aspects, and advantages of the present disclosure will become better understood regarding the following description, appended claims, and accompanying drawings.

FIG. 8 is a side view of a walker including a NPWT system according to another embodiment, with the dorsal shell and insole removed for ease of reference.

FIG. 9 is a front isometric view of the walker shown in FIG. 8.

DETAILED DESCRIPTION OF VARIOUS EMBODIMENTS

Figure 1:
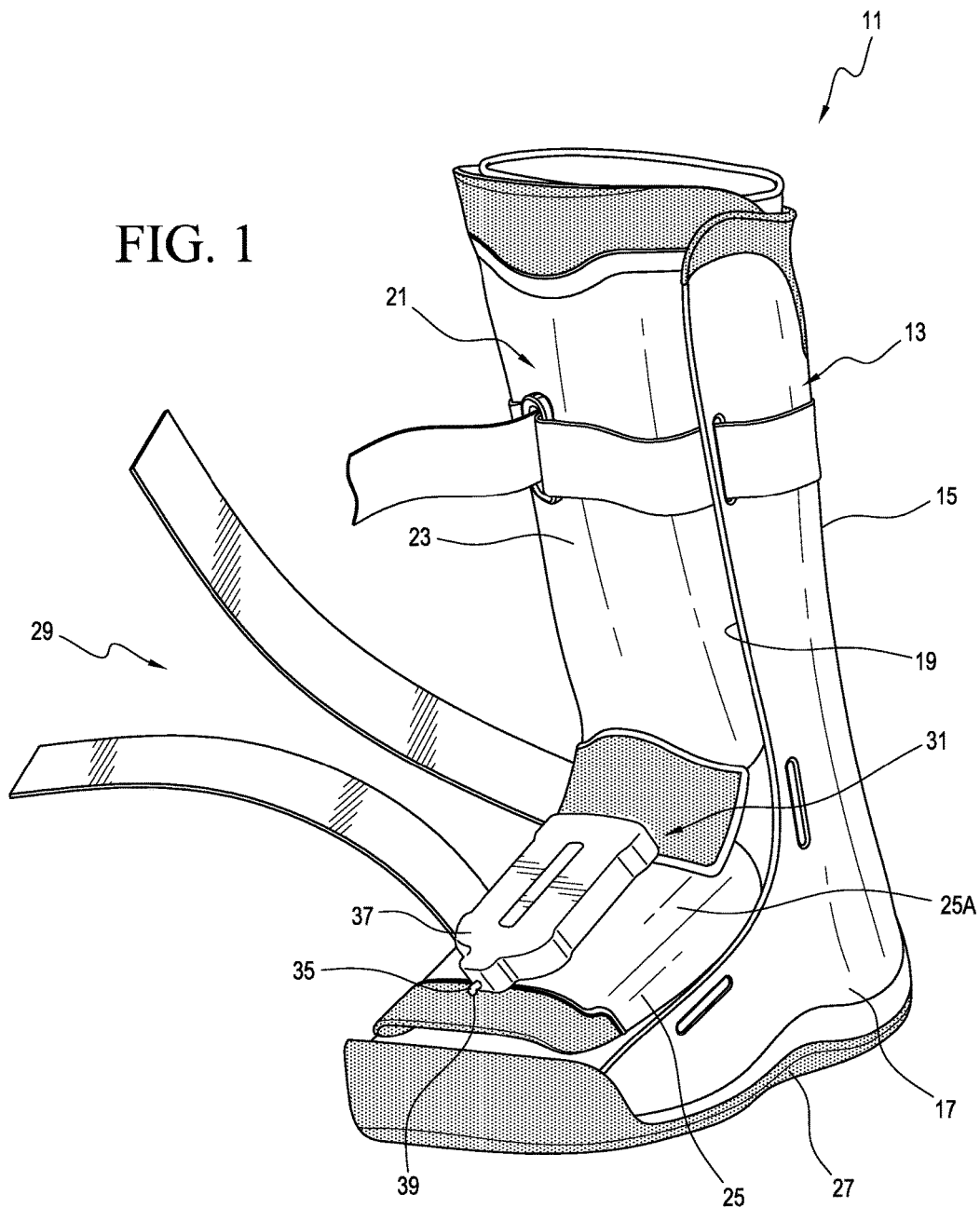
FIG. 1 is a front isometric view of a walker including a NPWT system according to an embodiment.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and described below. It should be understood, however, there is no intention to limit the disclosure to the embodiments disclosed, but on the contrary, that the intention covers all modifications, alternative constructions, combinations, and equivalents falling with the spirit and scope of the disclosure.

For further ease of understanding the embodiments of an orthopedic device as disclosed herein, a description of a few terms is necessary. As used herein, the term "dorsal" has its ordinary meaning and refers to the top surfaces of the foot, ankle and foreleg or shin. As used herein, the term "plantar" has its ordinary meaning and refers to a bottom surface, such as the bottom of a foot. As used herein, the term "proximal" has its ordinary meaning and refers to a location that is closer to the heart than another location. Likewise, the term "distal" has its ordinary meaning and refers to a location that is further from the heart than another location. The term "posterior" also has its ordinary meaning and refers to a location that is behind or to the rear of another location. Lastly, the term "anterior" has its ordinary meaning and refers to a location that is ahead of or to the front of another location.

The terms "rigid," "flexible," and "resilient" may be used herein to distinguish characteristics of portions of certain features of the orthopedic device. The term "rigid" is intended to denote that an element of the device is generally devoid of flexibility. Within the context of support members or shells that are "rigid," it is intended to indicate that they do not lose their overall shape when force is applied, and that in fact they may break if bent with sufficient force. On the other hand, the term "flexible" is intended to denote that features are capable of repeated bending such that the features may be bent into retained shapes or the features do not retain a general shape, but continuously deform when force is applied. The term "resilient" is used to qualify such flexible features as generally returning to an initial general shape without permanent deformation. As for the term "semi-rigid," this term is used to connote properties of support members or shells that provide support and are free-standing; however, such support members or shells may have some degree of flexibility or resiliency.

The exemplary embodiments of the NPWT orthopedic device can include configurations of walkers or walking boots, post-surgical shoes, or any other suitable orthopedic device.

First Embodiment of the NPWT Orthopedic Device

FIG. 1 shows a first embodiment of the NPWT orthopedic device comprising a walker 11 and a NPWT system 31 integrated into the walker 11. The walker 11 includes a base shell 13 and a dorsal shell 21. The base shell 13 includes a posterior portion 15 and a plantar portion 17 arranged to extend along the plantar surface of a user's foot. The base shell 21 defines an opening 19 over a dorsal aspect thereof.

The dorsal shell 21 is contoured to generally correspond to the opening 19 of the base shell 13, such that the lower leg of the user is generally fully enclosed and supported by the walker 11. The dorsal shell 21 is moveable away and towards the base shell 13 in order to open and close the walker 11. The dorsal shell 21 includes a proximal section 23 and a distal section 25.

An insole can be situated in a foot bed of the walker 11. As seen, an outsole 27 can be provided along the plantar portion 17 of the base shell 13. A plurality of tightening mechanisms 29 are arranged to bring the base shell 13 and the dorsal shell 21 closer together for tightening the walker 11 around the lower leg, ankle, and foot. The tightening mechanism 29 can include an ankle strap, an upper strap, and a foot strap. While a circumferential walker is shown, it will be appreciated that other walkers (e.g., a strut walker) may utilize similar configurations.

The NPWT system 31 includes a pump mechanism 37 secured to an upper surface 25A of the distal section 25 of the dorsal shell 21 and a wound covering (see e.g., wound covering 101 shown in FIG. 4) situated inside of the base shell 13 and arranged to form a sealed volume over a wound area of the user. The wound covering is fluidly connected to the pump mechanism 37 via a conduit 35. A tube hole 39 can be formed in the distal member 25 of the dorsal shell 21 for receiving the conduit 35 extending from the pump mechanism 37. The shape of the tube hole 39 can be generally complementary to the shape of the conduit 35. The conduit 35 extending from the pump mechanism 37 is threaded from the exterior of the walker 11 through the tube hole 39. From the tube hole 39, the conduit 35 is guided or routed within the interior of the walker 11 to the wound covering.

The pump mechanism 37 includes a negative pressure source and is arranged to apply a negative pressure to the wound area under the wound covering through the conduit 35. The negative pressure generated by the pump mechanism 37 over the wound area can draw wound exudate and/or other secretions away from the wound area through the conduit 35 into a collection unit, helping to accelerate healing. To help maintain the negative pressure over time, the wound covering may include an adhesive that forms a fluidly tight seal with the skin surrounding the wound area.

As seen, the pump mechanism 37 of the NPWT system 31 can be generally centered over the user's foot on the distal section 25 of the dorsal shell 21 and dimensioned not to increase a width of either the medial or lateral aspects of the walker 11. This is advantageous because additional width on the medial aspect of a walker can result in injuries to the user's contralateral limb, or can result in knee or hip issues from user's avoiding contact with the contralateral limb during gait. Furthermore, adding additional width on the lateral aspect of a walker can be cumbersome for users when they are resting in their side.

The pump mechanism 37 is also generally stacked or centered over a midline of the foot, decreasing the perceived added weight from the pump mechanism 37. The location of the pump mechanism over the foot also reduces moments on the foot about the ankle from the pump mechanism 37, making it easier for users with low muscle tone to lift the foot within the walker 11 during gait, for example, when climbing stairs of walking up a ramp.

By arranging the pump mechanism 37 on the distal section 25 of the dorsal shell 21, the distance between the pump mechanism 37 and the wound area is generally constant and shortened as compared to an external vacuum source being carried near the hip or on other parts of the user's body as in the prior art, reducing the likelihood of the conduit 35 being tangled or caught during use.

This also reduces and stabilizes the effects of fluid head height within the NPWT system 31 that can compete against the negative pressure applied to the wound area by the pump mechanism 37. This is advantageous as NPWT is typically delivered at relative low vacuum pressures such as, for example, between about −75 and −150 mmHg. The vacuum source of known NPWT systems is commonly positioned at or near the waist of a user, which can be roughly 29 inches above a wound area on the plantar aspect of the foot. This height difference or fluid head height in the NPWT system, if not accounted for, can yield a vacuum reduction of about 55 mmHg, effectively reducing a vacuum of −75 mmHg to about −20 mmHg. It will be appreciated that a vacuum of less than −40 mmHg is known to be less effective in providing healing.

Furthermore, fluid head height created by a vacuum source that is carried at or near the waist can vary with movement of the foot or lower leg relative to waist, which, in turn, can drastically or detrimentally impact negative pressure applied to the wound area, reducing the effectiveness and reliability of the NPWT system. Embodiments of the NPWT system thus beneficially position the pump mechanism 37 near the wound area, reducing and stabilizing potentially counterproductive fluid head height within the NPWT system 31.

Placing the pump mechanism 37 on the upper surface of the dorsal shell 21 also improves the accessibility of the NPWT system 31, as it allows the pump mechanism 37 to be easily and readily monitored by patients who are responsible for providing or assisting with their own care. The NPWT system 31 is thus more effective and easier to use for a user than known NPWT systems.

It will be appreciated that the NPWT system 31 can be disposable and can comprise any suitable system. For instance, the pump mechanism 37 and/or the wound dressing can be arranged for single use and can be easily exchanged with replacement components. The pump mechanism 37 can be a vacuum pump, a powered negative pressure source, a manually powered negative pressure source, a suction bulb, and/or any other suitable type of negative pressure source. The pump mechanism 37 can comprise an electro-mechanical pump mechanism. The pump mechanism 37 can be independently operable such that it can create and/or maintain a vacuum during periods of low or no activity for patients who are notoriously non-compliant to therapy protocols.

In an embodiment, the conduit 35 has a flattened configuration, helping to limit or prevent pressure points or lines associated within the conduit 35 pressing against the user's skin or foot within the walker 11. The conduit 35 can include one or more tubes. According to a variation, a collection unit can be integrated with the pump mechanism 37. The collection unit may be located along a length of the conduit 35 before the pump mechanism 37, or may be located elsewhere relative to the pump mechanism 37. In other embodiments, one or more filters and/or valves may be included in the NPWT system 31 to control or limit flow along the vacuum pathway, for example, at an outlet of the pump mechanism 37.

In other embodiments, the collection unit can be a separate, replaceable unit from the pump mechanism 37. This can allow the collection unit to be accessible such that it can be more easily monitored and/or replaced. For instance, the collection unit can be located on the interior of the walker 11 and can be inserted and/or removed through an opening formed in the dorsal shell 21, allowing the collection unit to be removed without removing the dorsal shell 21. This may be particularly advantageous for patients who cannot remove the dorsal shell because of a compliance strap securing the dorsal shell to the base shell. In other embodiments, the collection unit can be inserted and/or removed from the interior of the walker via an opening formed in the base shell 21.

The wound covering can be a flexible cover including one or more pre-cut apertures or a wound dressing. Optionally, the wound covering can include a wound packing material.

According to a variation, at least one indentation or groove can be formed within the interior surface of the walker 11 for guiding the conduit 35 to the wound covering. The groove can be formed on the dorsal shell 21 and/or the base shell 13 and can exhibit any suitable configuration. Routing the conduit 35 through the groove on the interior of the walker 11 can help reduce or eliminate pressure points on the interior of the walker 11, which can be both uncomfortable as well as a risk for resulting in pressure ulcers. Guiding the conduit 35 in the groove can also protect the conduit 35 from being inadvertently crushed or pinched. The conduit 35 can be uncovered or covered or secured in the groove using adhesive tape, a separate cover component, or any other suitable means. The conduit 35 can be flexible so that the conduit 35 can generally conform to the contour of the walker 11.

Second Embodiment of the NPWT Orthopedic Device

Figure 2:
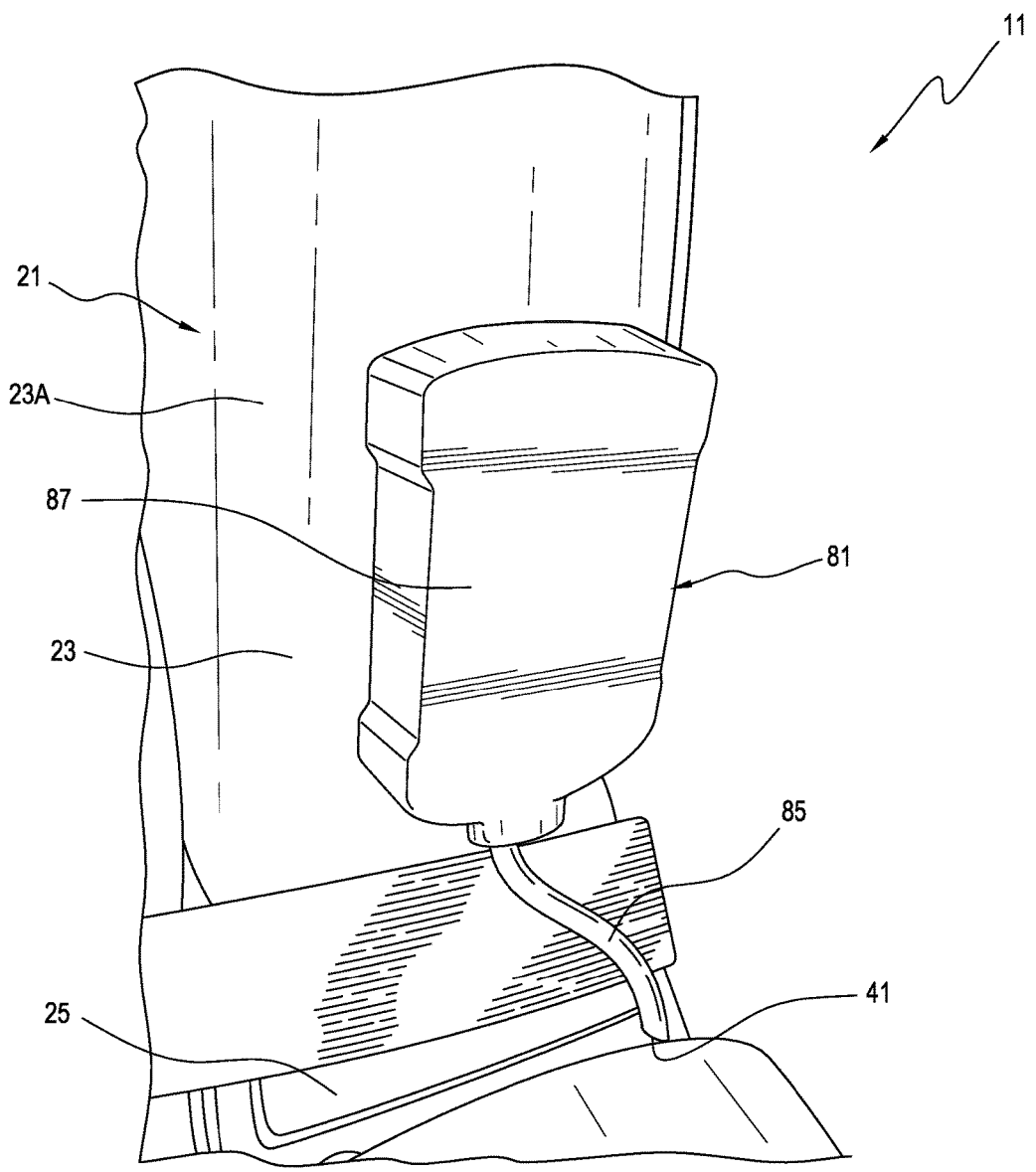
FIG. 2 is a partial front isometric view of a walker including a NPWT system according to another embodiment.

FIG. 2 shows another embodiment of the NPWT orthopedic device comprising a walker 11 and a NPWT system 81 including a pump mechanism 87. The pump mechanism 87 in this embodiment is secured to the outer surface 23A of the proximal section 23 of the dorsal shell 21. A tube hole 41 can be formed in the distal section 25 for receiving a conduit 85 extending from the pump mechanism 87. The conduit 85 extending from the pump mechanism 87 can be threaded from the exterior of the walker 11 through the tube hole 41 and to a wound covering within the walker 11.

As seen the pump mechanism 87 is located on the proximal section 23 at or near a strap extending across the ankle and the user's foot. By placing the pump mechanism 37 on the anterior aspect of the walker 11 just above the foot, the fluid head height within the NPWT system 81 is reduced. In addition, weight distribution of the walker 11 can be improved because the weight of the pump mechanism 87 is supported by the lower leg of the user rather than on the foot. This is beneficial because the pump mechanism 87 does not generate a moment on the foot about the ankle, reducing the likelihood of user fatigue due to the incorporation of the NPWT system 81.

Third Embodiment of the NPWT Orthopedic Device

Figure 3:
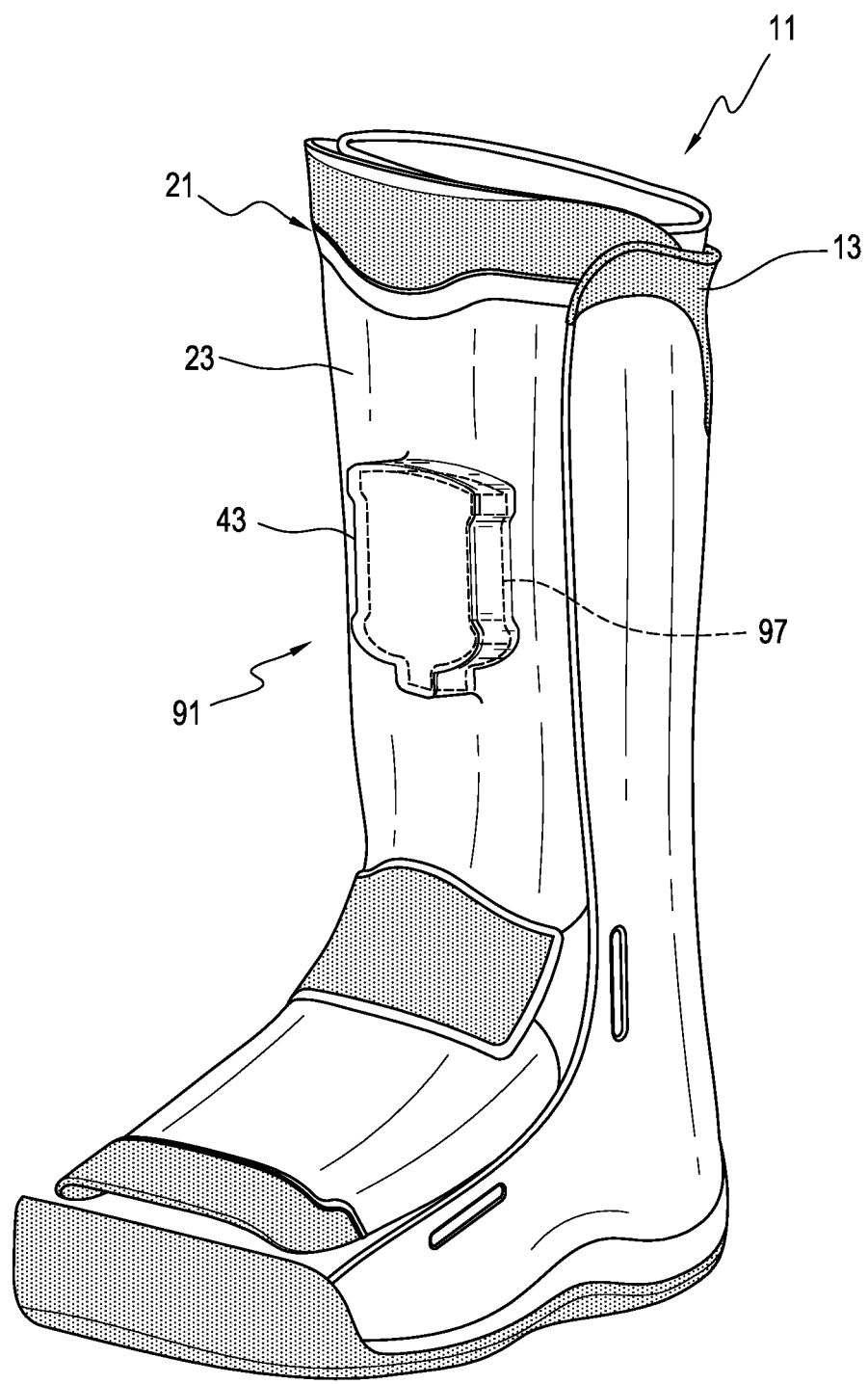
FIG. 3 is a front isometric view of a walker including a NPWT system according to another embodiment.
Figure 4:
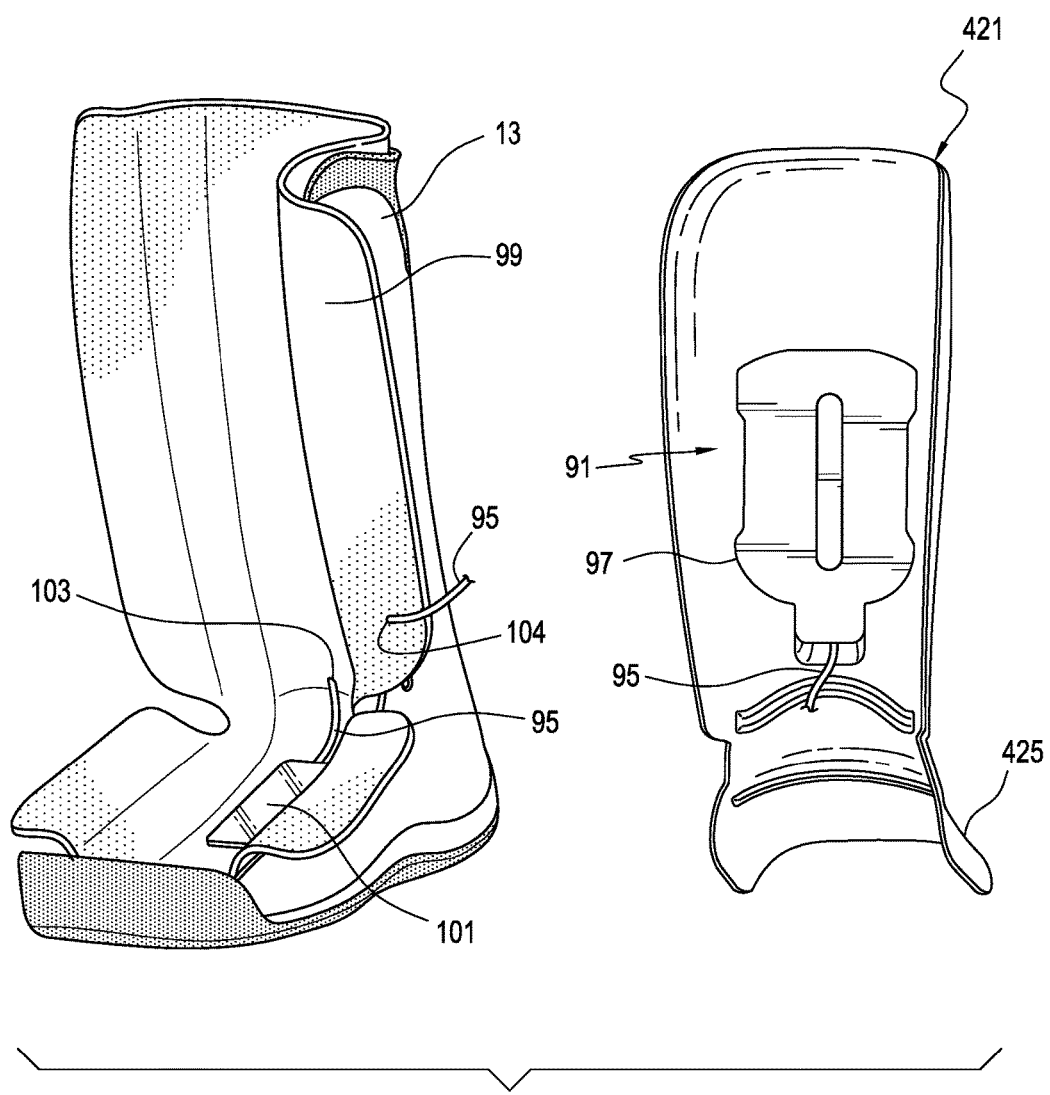
FIG. 4 is a partially exploded view of the walker of FIG. 3 showing the NPWT system.
Figure 5:
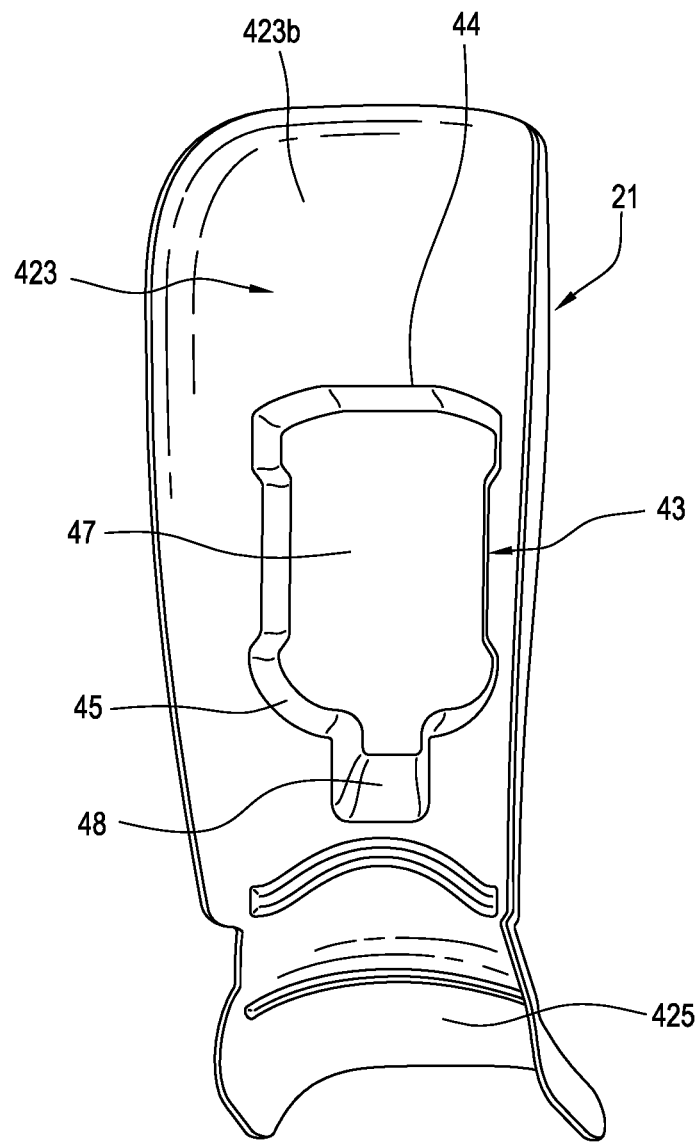
FIG. 5 is a back view of the dorsal shell shown in FIG. 3.

FIGS. 3-5 show another embodiment of the NPWT orthopedic device comprising a walker 11 and a NPWT system 91 including a pump mechanism 97 positioned in a receiving space 43 on a dorsal shell 421. FIGS. 3-5 do not show the tightening members or straps for ease of reference. The dorsal shell 421 includes a proximal section 423 and a distal section 425.

The receiving space 43 is defined along an inner surface 423B of the proximal section 423 over the lower leg of the user. The receiving space 43 can be defined along a length of the proximal section 423 arranged to be between an upper strap member and an ankle strap member arranged to extend over the ankle of the user. The receiving space 43 can be defined along a length of the proximal section 423 below the upper strap member.

The receiving space 43 is sized and configured to house the pump mechanism 97. As seen, the receiving space 43 extends outwardly from the inner surface 423B of the proximal section 423 so that the pump mechanism 97 can fit within the receiving space 43 without substantially impact the space within the walker 11.

Similar to the previously described embodiments, the location of the pump mechanism 97 on the proximal section 423 reduces and stabilizes the effects of fluid head height within the NPWT system 91 by shortening and keeping the distance between the pump mechanism 97 and a wound area generally constant. It also does not increase a width of the medial or lateral aspects of the walker 11, reducing the likelihood of discomfort or injuries to the user due to the pump mechanism 97. The location of the pump mechanism 97 can also decrease the perceived weight of the pump mechanism 97 and reduce or eliminate moments on the foot from the pump mechanism 97 about the user's ankle.

By arranging the pump mechanism 97 within the receiving space 43, the pump mechanism 97 is located inside the walker 11 during use and protected from damage due to accidental contact with external objects. This also reduces the likelihood of tampering or unintended inference with the pump mechanism 97.

Arranging the pump mechanism 97 within the receiving space 43 also beneficially allows the walker 11 to be removed from the foot without having to disconnect the NPWT system 91. For example, as shown in FIG. 4, the NPWT system 91 includes the pump mechanism 97 removably secured in the receiving space 43 and a wound covering 101 situated inside of the base shell 13 on a soft goods liner 99. The liner 99 has foam padding and provides as an interface between the user's anatomy and the walker 11.

The wound covering 101 is fluidly connected to the pump mechanism 97 via a conduit 95 comprising a tube having a flattened configuration. A portion of the tube 95 extending from the pump mechanism 97 is threaded through a first opening 103 in the ankle area of the liner 99 and routed through a thickness of the liner 99 toward the wound covering 101 where the tube 95 exits from the liner 99 from a second opening 104. As such, the user's foot can be removed from the walker 11 without disconnecting the NPWT system 91. In addition, the liner 99 can be easily removed from the walker 11 with the NPWT system 91 intact, making the system more usable. Optionally, the tube 95 can be removably attached to the wound covering 101 and/or the pump mechanism 97 such that the wound covering 101 and/or pump mechanism 97 can be removed or cleaned without having to remove the tube 95 from the liner 99.

Referring to FIG. 5, the receiving space 43 is integral to the proximal section 423. The proximal section 423 includes an access or pump opening 44 and a peripheral sidewall 45 extending from the access opening 44 to a distance beyond the outer surface of the proximal section 423. A closed bottom 47 extends between the peripheral sidewall 45 above the outer surface of the proximal section 423. The receiving space 43 is bounded by the peripheral sidewall 45 and the closed bottom 47. The peripheral sidewall 45 can be continuous or non-continuous.

The receiving space 43 can be sized and shaped such that an interference fit is created between the pump mechanism 97 and the receiving space 43. In other embodiments, the pump mechanism 37 can be secured within the receiving space 43 by adhesives, snaps, fasteners, hook-and-loop type systems, or any other suitable connection systems.

Optionally, a distal portion of the peripheral sidewall 45 can include a ramped surface 48 adapted to help guide the conduit 95 extending from the pump mechanism 37 toward the wound covering 101 as the conduit exits the pump mechanism 37.

Fourth Embodiment of the NPWT Orthopedic Device

Figure 6:
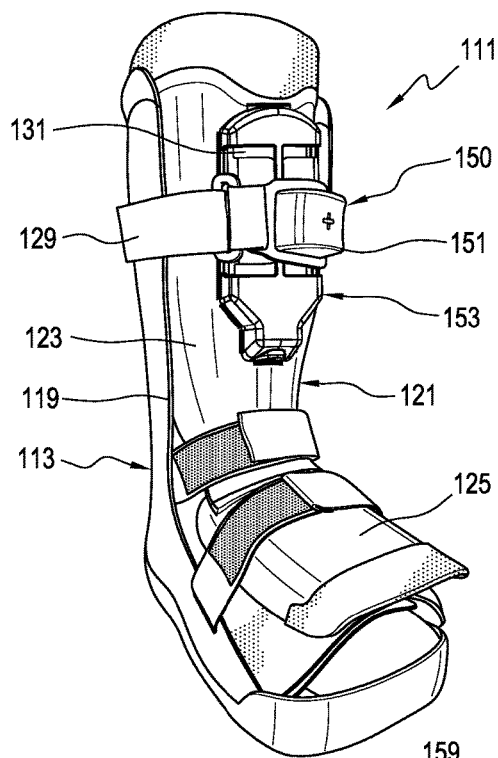
FIG. 6 is a front isometric view of a walker including a NPWT system according to another embodiment.
Figure 7:
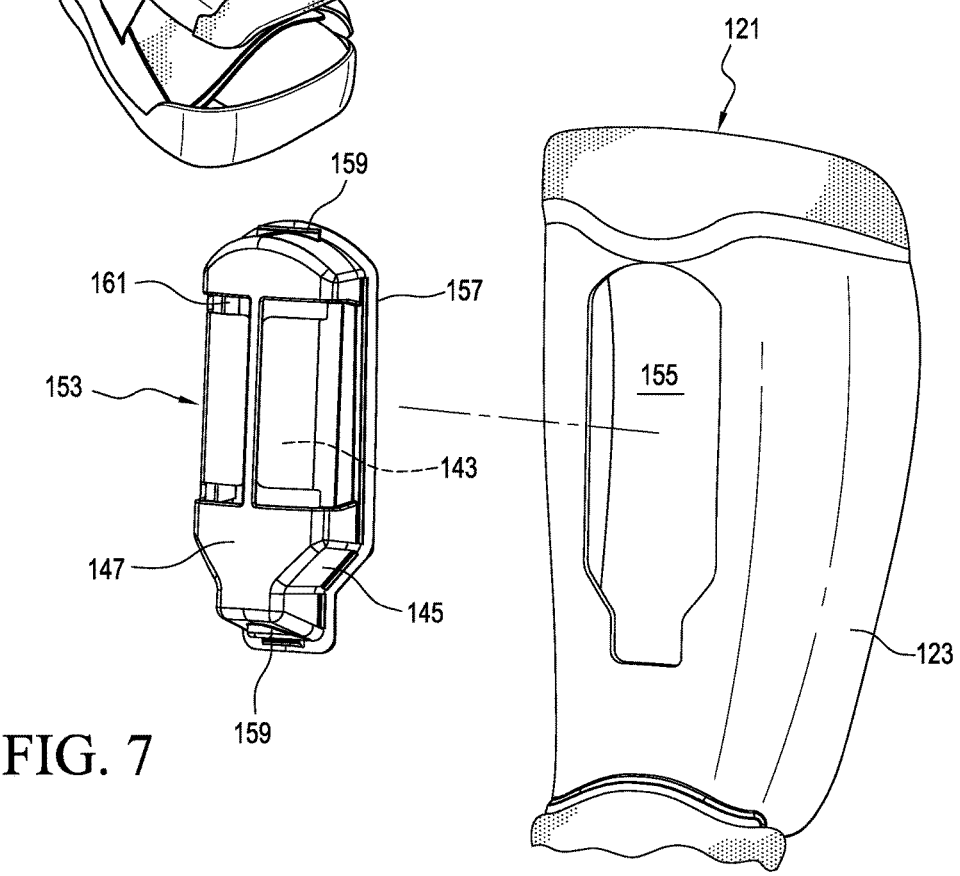
FIG. 7 is an exploded view of the dorsal shell shown in FIG. 3.

FIGS. 6 and 7 show another embodiment of the NPWT orthopedic device comprising a walker 111 and a NPWT system 131. The walker 111 includes a base shell 113 defining an opening 119 over a dorsal aspect thereof and a dorsal shell 121. The dorsal shell 121 includes a proximal section 123 and a distal section 125 and is contoured to generally correspond to the opening 119 of the base shell 113. A plurality of straps 129 are arranged to bring the base shell 113 and the dorsal shell 121 closer together for tightening the walker 111 around the lower leg, ankle, and foot.

Optionally, the walker 111 can include an inflation system 150 arranged to reduce pressure points within the walker 111, accommodate different sized anatomies, and/or to accommodate swelling. The inflation system 150 includes a pump assembly 151 situated on the upper strap 129 and arranged to inflate at least one inflatable bladder disposed in the base shell 113.

A receiving space 143 on the dorsal shell 121 is arranged to house a pump mechanism of the NPWT system 131. The receiving space 143 can be similar to the receiving space 43 except that it is at least part defined by a cover member 153 removably attached to the proximal section 123.

As seen in FIG. 7, a cutout 155 is defined in the proximal section 123. The cover member 153 is sized and configured to engage the cutout 155 and includes a peripheral sidewall 145 extending from the cutout 155 to a distance beyond the outer surface of the proximal section 123. The cover member 153 includes a closed bottom 147 that extends between the peripheral sidewall 145 above the outer surface of the proximal section 123. The closed bottom 147 can define one or more observation holes 161, allowing for visual observation of the pump mechanism within the receiving space 143. The receiving space 143 is bounded by the peripheral sidewall 145 and the closed bottom 147 of the cover member 153.

The cover member 153 can be attached to the proximal section 123 over the cutout 155 in any suitable manner. The cover member 153 can be secured to the proximal section 123 via a snap-type connection. The cover member 153 can be secured to the proximal section 123 via a peripheral flange 157 arranged to engage the inner surface of the proximal section 123 and upper and lower protrusions 159 arranged to engage the outer surface of the proximal section 123 opposite the flange 157.

The cover member 153 can be detached from the outside of the walker 111, providing access to the pump mechanism from the outside of the walker 111. This beneficially allows the pump mechanism to be removed, replaced, and/or maintained without having to remove the walker 111 from the user's leg.

Optionally, the upper strap 129 can be arranged to extend over the closed bottom 147 of the cover member 153 to help secure the cover member 153 on the proximal section 123 over the cutout 155. Alternatively, the cover member 153 can be removably attached to the proximal section 123 via fasteners, hook-and-loop type systems, clips, magnets, or any other suitable attachment system.

By arranging the pump mechanism within the cutout 155 and the cover member 153, the pump mechanism can be protected from damage due to accidental contact with external objects. Moreover, the cover member 153 can help limit or eliminate pressure points from pump mechanism.

Fifth Embodiment of the NPWT Orthopedic Device

FIGS. 8 and 9 show another embodiment of the NPWT orthopedic device comprising a walker 211 and a NPWT system 231 including a pump mechanism 49 located along the posterior aspect of the base shell 213. The dorsal shell, liner, straps, and insole are removed from the walker 211 for ease of reference.

The pump mechanism 49 is located on the posterior aspect of the base shell 213 about halfway up a height of the walker 211. By arranging the pump mechanism 49 on the posterior aspect of the base shell 213, the pump mechanism 49 does not interfere with dorsal shell placement or from accessing the straps. In addition, the location of the pump mechanism 49 reduces and stabilizes the effects of fluid head height within the NPWT system 231 by shortening and keeping the distance between the pump mechanism 49 and the wound area generally constant. It also does not increase a width of the medial or lateral aspects of the walker 211, reducing the likelihood of discomfort or injuries to the user due to the pump mechanism 49.

As seen, a top surface of the pump mechanism 49 is spaced a distance from the proximal edge of the base shell 213 forming a clearance between the pump mechanism 49 and the proximal edge such that the pump mechanism 49 does not interfere with the posterior thigh during flexion.

The pump mechanism 49 is secured to the base shell 213 via a clip member 51 formed on the pump mechanism 49. The clip member 51 includes a proximal end section 55 and a distal section 57. The proximal end section 55 is attached to the pump mechanism 49 and the distal section 57 includes a free end. The distal section 57 is formed so as to bias the clip member 51 toward the outer surface of the pump mechanism 49. In other embodiments, the pump mechanism 49 can be secured to the posterior portion 215 via a cover member, a hook-and-loop type system or the like.

A cutout 53 is formed in the posterior portion 215 that extends completely between the interior and exterior surfaces of the base shell 13. The cutout 53 can have any suitable configuration. The clip member 51 can be inserted through the cutout 53 such that the posterior portion 215 of the base shell 213 can be secured between the inner surface of the clip member 51 and the outer surface of the pump mechanism 49. Through the structure of the clip member 51 and the pump mechanism 49, the pump mechanism 49 has the benefit of being easily and quickly removed from the base shell 13. According to a variation, the cutout 53 can provide at least in part a housing for other components of the walker 211 (e.g., air system valves).

A conduit 235 extends downwardly from the distal end section of the pump mechanism 49 along the exterior surface of the posterior portion 215, reducing the likelihood of a pressure point from the conduit 235 as the patient walks in the walker 211 and the likelihood of the conduit 235 being pinched or kinked inside of the walker 211.

The posterior portion 215 of the base shell 213 includes a tube hole 61 that allows the conduit 235 to pass from the exterior surface of the posterior portion 215 to the interior surface of the base shell 213 such that the conduit 235 can connect to a wound covering 233 within the walker 211.

At least one indentation or groove 51 can be formed within the interior surface of the base shell 213 for guiding the conduit to the cover 233. The groove 51 can be any suitable configuration. For instance, the groove 51 can extend from the tube hole 61 to a point below the upper surface of the cover 233. Routing the conduit 235 through the groove 51 on the interior of the base shell 213 can help reduce or eliminate pressure points on the interior of the walker 211, which can be both uncomfortable as well as a risk for resulting in pressure ulcers. Guiding the conduit 235 in the groove 51 can also protect the conduit 235 from being inadvertently crushed or pinched. The conduit 235 can be uncovered or covered or secured in the groove 51 using adhesive tape, a separate cover component, or any other suitable means.

In other embodiments, the pump mechanism 49 can be located within a receiving space formed on the interior surface of the posterior portion 215 of the base shell 213. In other embodiments, the pump mechanism 49 can be positioned under a cover member attached to the posterior portion 215 of the base shell 213, protecting the pump mechanism for inadvertent damage or tampering.

Sixth Embodiment of the NPWT Orthopedic Device

Figure 10:
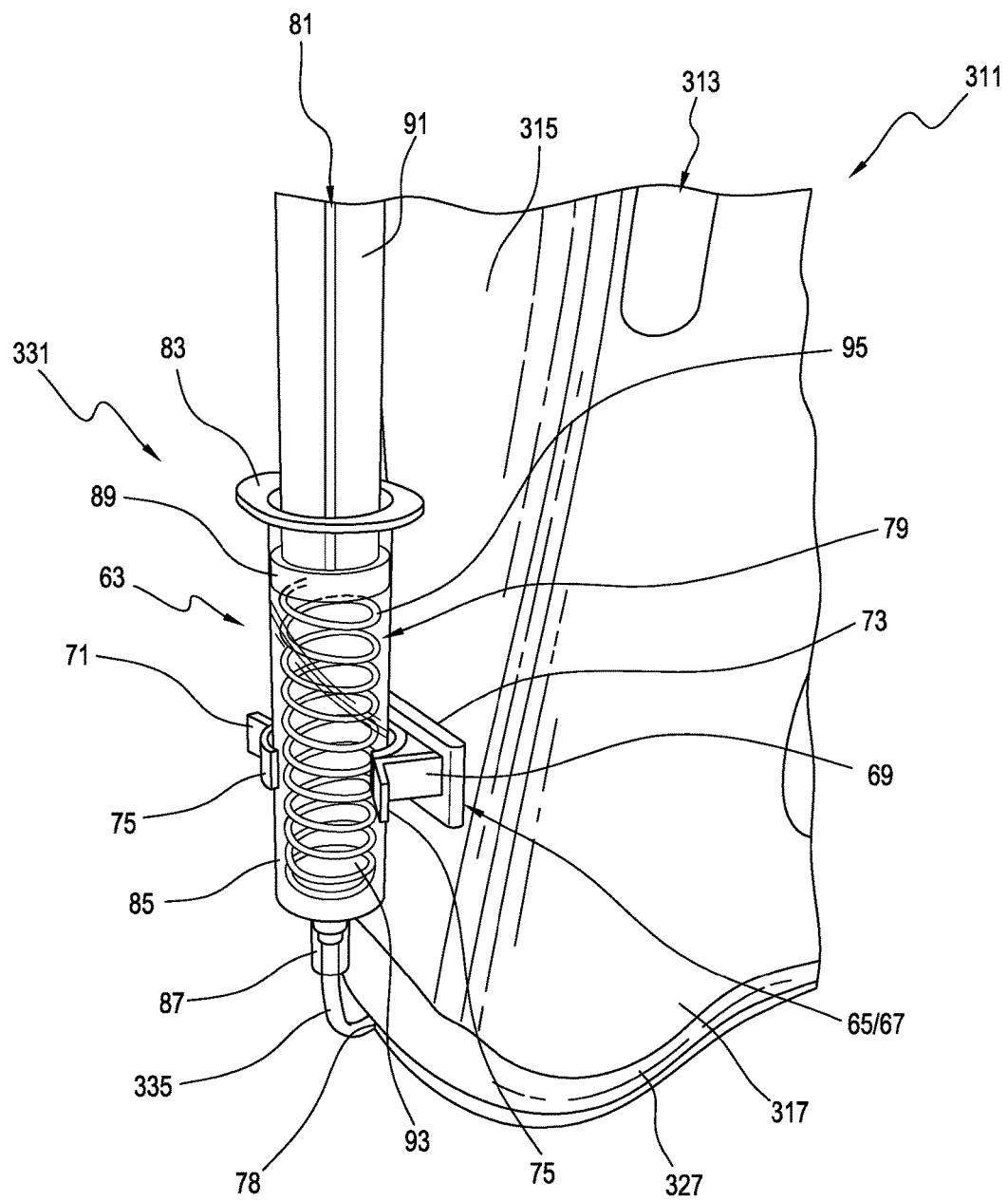
FIG. 10 is a back isometric view of a walker including a NPWT system according to another embodiment.

FIG. 10 shows another embodiment of the NPWT Orthopedic Device comprising a walker 311 and a NPWT system 331 having a pump mechanism 63 located along the posterior aspect of the base shell 313 and attached to the posterior portion 315 via an attachment system 65 that allows the pump mechanism 63 to be removably attached to the base shell 313.

The attachment system 65 can include a clip 67 having a first arm 69, a second arm 71, and a base 73. The first and second arms 69 and 71 each define an engagement surface and are spaced at a distance less than the diameter of an outer surface of body of the pump mechanism 63. The engagement surfaces can form a shape that generally complements the shape of the body of the pump mechanism 63. Each arm 69, 71 further includes a retaining section 75 that protrudes from a free end of its engagement surface. At least one of the retaining sections 75 protrudes toward the opposite engagement surface, thereby narrowing the distance between the engagement surfaces.

The base 73 connect the ends of the arms opposite the retaining sections 75, and holds these ends in a substantially rigid position with respect to each other, such that the engagement surfaces of the clip 67 will resiliently engage the pump mechanism 63 when the arms 69, 71 are received over the body of the pump mechanism 63. The retaining sections 75 narrow the opening between the free ends of the arms, and are arranged to prevent unforced radial removal of the pump mechanism 63 from the clip 67.

The conduit 335 can extend downwardly from the distal end section of the pump mechanism 63 to a tube hole 78 formed at or near the plantar portion 317 of the base shell 313. The tube hole 78 can extend through the outsole 327 and allows the conduit 335 to pass from the exterior surface of the posterior portion 315 to the interior surface of the walker 311 such that the conduit 335 can connect to the wound covering within the walker.

As noted above, the NPWT system can be any suitable system. For instance, the pump mechanism 63 shown in FIG. 10 can include a body 79 and a plunger or push rod assembly 81 that extends within and is movable relative to the body 79. The body 79 can include a cylindrical barrel 85 and a nozzle 87. The nozzle 87 can include a port, providing a means of connection such as a luer fitting or other fluid connector.

A conduit 335 can be removably coupled to the nozzle 87 and a valve or filter creating a fluid connection between the barrel 85 and a wound covering. The valve can seal the conduit 335 when the pump mechanism 63 is removed from the conduit 335, reducing the likelihood of contamination or infection.

The plunger assembly 81 can include a plunger head 89 and a plunger rod 91 that extends from the plunger head 89. The plunger rod 91 can extend beyond an end of the body 79. The end of the plunger rod 91 that extends beyond the body 79 may include an appropriate actuation feature for engagement by a patient or another person such that the patient or someone else can manually actuate the pump mechanism 63.

One or more sealing surfaces may be formed on the perimeter of the plunger head 89 that engage the interior wall of the barrel 85. The interface between the perimeter of the plunger head 89 and the interior wall of the barrel 85 defines at least one seal between the plunger head 89 and the barrel 85. A fluid chamber 93 is defined between the bottom surface of the plunger head 89 and the nozzle 87.

When the plunger assembly 81 is moved away from the nozzle 87, the volume of the fluid chamber 93 increases, which, in turn, creates a vacuum or negative pressure inside of the fluid chamber 93. This negative pressure can draw exudate or other fluid into the fluid chamber 93 through the conduit 335 and from the vacuum reservoir formed over the wound by the wound covering. As seen, the barrel 85 can be generally translucent, allowing for observation of fluid in the fluid chamber 93. In other embodiments, the barrel 85 can include a translucent window for observation of fluid in the fluid chamber 93.

With the exudate in the fluid chamber 93, the pump mechanism 63 can be decoupled from the conduit 335 and removed from the attachment system 65 for disposal. Optionally, the plunger assembly 81 of the decoupled pump mechanism 63 can be moved toward the nozzle 87, reducing the volume of the fluid chamber 93 such that fluid within the fluid chamber 93 is discharged or expelled out of the nozzle 87 for disposal or sampling.

A resilient member or internal compression spring 95 can be situated in the fluid chamber 93. The spring 95 can apply a force or pressure to the plunger head 89 in a direction away from the nozzle 87, creating a vacuum in the fluid chamber 93. The amount of vacuum created by the spring 95 can be adjusted or selected by controlling the force provided by the spring 95 on the plunger head 89 over the cross-sectional area of the barrel 85. The spring 95 can be a constant force spring. The spring 95 can be a low-force compression spring.

The pump mechanism 63 is shown including a single barrel and plunger assembly but can also include two or more barrels and plunger assemblies, decreasing the overall length of the pump mechanism 63 required to generate a specific fluid collection volume. The pump mechanism 63 can further include two barrels, each including a spring or a coupler to connect each of the barrels to a common spring. This can help create consistency of vacuum pressure between the barrels. Further, the body 79 is described including a single port but may include any number of ports. For instance, the body 79 may include an inlet port and an outlet port, each associated with a one-way valve to control the direction of fluid flow. The inlet one-way valve only allows fluid to enter the fluid chamber 93 and is connected to the conduit 335. The outlet one-way valve only allows fluid to be expelled out of the fluid chamber 93.

While one conduit is described, it will be appreciated that the NPWT system of present disclosure can include two, three, or any other suitable number of conduits. In other embodiments, the conduit can comprise channels formed within the walls of the walker that provide fluid communication between the pump mechanism and the cover. In yet other embodiments, the NPWT system can include two, three, or any other suitable number of pump mechanisms. In other embodiments, a collection unit can be incorporated into the structure of the walker. In other embodiments, the pump mechanism can be attached to the anterior or posterior aspect of the tightening members or straps 29.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. A negative pressure wound therapy (NPWT) orthopedic device comprising:
a base shell having a posterior portion and a plantar portion, the base shell defining an opening over a dorsal aspect thereof;
a dorsal shell contoured to generally correspond to the opening of the base shell, the dorsal shell including a proximal section and a distal section, the proximal section at least in part defining a receiving space; and
a NPWT system including a pump mechanism secured in the receiving space, a wound covering situated inside of the base shell and arranged to form a sealed volume over a wound area of a user, and at least one conduit forming a fluid connection between the wound covering and the pump mechanism, wherein the pump mechanism is arranged to apply a negative pressure to the wound area through the at least one conduit;
wherein a cutout is formed in the dorsal shell and the receiving space is defined by a cover member removably attached over the cutout.

2. The NPWT orthopedic device of claim 1, wherein the cover member is arranged to snap into the cutout.

3. The NPWT orthopedic device of claim 1, wherein the cover member is at least in part secured over the cutout by an upper strap member extending over the cover member and arranged to hold the dorsal shell and the base shell together.

4. The NPWT orthopedic device of claim 1, wherein the peripheral sidewall and closed bottom of the receiving space are integral to the dorsal shell.

5. The NPWT orthopedic device of claim 1, wherein the pump mechanism is removably secured in the receiving space.

6. The NPWT orthopedic device of claim 1, wherein the receiving space defines a ramped surface adapted to guide a portion of the at least one conduit exiting the pump mechanism toward the wound covering.

7. The NPWT orthopedic device of claim 1, wherein the at least one conduit comprises a tube having a flattened configuration.

8. The NPWT orthopedic device of claim 1, further comprising a liner disposed in the base shell, at least a portion of the at least one conduit being routed within a thickness of the liner.

9. The NPWT orthopedic device of claim 1, wherein the pump mechanism is removable from an exterior of the NPWT orthopedic device.

10. A negative pressure wound therapy (NPWT) orthopedic device comprising:

a base shell having a posterior portion and a plantar portion, the base shell defining an opening over a dorsal aspect thereof;

a dorsal shell contoured to generally correspond to the opening of the base shell, the dorsal shell including a proximal section and a distal section, the proximal section at least in part defining a receiving space; and a NPWT system including a pump mechanism secured in the receiving space, a wound covering situated inside of the base shell and arranged to form a sealed volume over a wound area of a user, and at least one conduit forming a fluid connection between the wound covering and the pump mechanism, wherein the pump mechanism is arranged to apply a negative pressure to the wound area through the at least one conduit;

wherein the receiving space includes a peripheral sidewall and a closed bottom;

wherein the closed bottom of the receiving space defines one or more observation holes.

11. A negative pressure wound therapy (NPWT) orthopedic device comprising:

a base shell having a posterior portion and a plantar portion, the base shell defining an opening over a dorsal aspect thereof;

a dorsal shell contoured to generally correspond to the opening of the base shell, the dorsal shell including a proximal section and a distal section, the proximal section at least in part defining a receiving space; and a NPWT system including a pump mechanism secured in the receiving space, a wound covering situated inside of the base shell and arranged to form a sealed volume over a wound area of a user, and at least one conduit forming a fluid connection between the wound covering and the pump mechanism, wherein the pump mechanism is arranged to apply a negative pressure to the wound area through the at least one conduit;

wherein the receiving space is sized and configured to form an interference fit between the pump mechanism in the receiving space and the dorsal shell.

* * * * *